United States Patent
Alig et al.

(10) Patent No.: US 8,722,717 B2
(45) Date of Patent: May 13, 2014

(54) 3-TRIAZOLYLPHENYL-SUBSTITUTED SULPHIDE DERIVATIVES AS ACARICIDES AND INSECTICIDES

(75) Inventors: Bernd Alig, Königswinter (DE); Stefan Antons, Leverkusen (DE); Reiner Fischer, Monheim (DE); Norbert Lui, Odenthal (DE); Adeline Köhler, Wuppertal (DE); Arnd Voerste, Köln (DE); Ulrich Görgens, Ratingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/859,350

(22) Filed: Aug. 19, 2010

(65) Prior Publication Data

US 2011/0046194 A1 Feb. 24, 2011

(30) Foreign Application Priority Data

Aug. 20, 2009 (EP) .................................... 09168284

(51) Int. Cl.
- *A01N 43/56* (2006.01)
- *A01N 43/653* (2006.01)
- *C07D 249/08* (2006.01)
- *C07D 231/12* (2006.01)

(52) U.S. Cl.
USPC ...... 514/383; 514/406; 548/262.2; 548/377.1

(58) Field of Classification Search
USPC ........................................... 548/262.2, 377.1
See application file for complete search history.

(56) References Cited

U.S. PATENT DOCUMENTS

| | | | |
|---|---|---|---|
| 6,509,354 B1 | 1/2003 | Toriyabe et al. | |
| 7,612,100 B2 | 11/2009 | Koyanagi et al. | |
| 2006/0281780 A1 | 12/2006 | Goto et al. | |
| 2008/0305955 A1 | 12/2008 | Bretschneider et al. | |
| 2009/0076282 A1 | 3/2009 | Toriyabe et al. | |
| 2009/0247551 A1 | 10/2009 | Jeschke et al. | |
| 2009/0253749 A1 | 10/2009 | Jeschke et al. | |
| 2010/0210704 A1 | 8/2010 | Ohata et al. | |
| 2010/0240705 A1 | 9/2010 | Jeschke et al. | |
| 2011/0015405 A1 | 1/2011 | Antons et al. | |
| 2011/0033432 A1 | 2/2011 | Davies et al. | |
| 2011/0045104 A1 | 2/2011 | Alig et al. | |
| 2011/0053996 A1 | 3/2011 | Andersch et al. | |
| 2011/0124588 A1 | 5/2011 | Jeschke et al. | |
| 2011/0166109 A1 | 7/2011 | Andersch et al. | |

FOREIGN PATENT DOCUMENTS

| | | | | |
|---|---|---|---|---|
| CA | 2 671 179 A1 | 6/2008 | | |
| EP | 0 539 588 A1 | 5/1993 | | |
| EP | 1 076 053 A1 | 2/2001 | | |
| EP | 1076053 A | * 2/2001 | ........... | C07D 249/08 |
| JP | 2007-284387 A | 1/2007 | | |
| JP | 2007-284356 A | 11/2007 | | |
| JP | 2007-284386 A | 11/2007 | | |
| WO | WO 99/55668 A | * 11/1999 | ........... | C07D 249/08 |
| WO | WO 99/55668 A1 | 11/1999 | | |
| WO | WO 2005/035486 A1 | 4/2005 | | |
| WO | WO 2006/043635 A1 | 4/2006 | | |
| WO | WO 2006/056433 A2 | 6/2006 | | |
| WO | WO 2006/100288 A2 | 9/2006 | | |
| WO | WO 2007/043677 A1 | 4/2007 | | |
| WO | WO 2007/057407 A2 | 5/2007 | | |
| WO | WO 2007/095229 A2 | 8/2007 | | |
| WO | WO 2007/149134 A1 | 12/2007 | | |
| WO | WO 2008/104503 A1 | 9/2008 | | |
| WO | WO 2009/051245 A1 | 4/2009 | | |

OTHER PUBLICATIONS

Patini et al., Chem. Rev., 1996, vol. 98(8), pp. 3147-3172.*
Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, SCI., Great Britain (1997).
English language Abstract of Japanese Patent Publication No. JP 2007-284356 A, Japanese Patent Office, Patent & Utility Model Gazette DB, Patent Abstract of Japan (2007).
English language Abstract of Japanese Patent Publication No. JP 2007-284386 A, Japanese Patent Office, Patent & Utility Model Gazette DB, Patent Abstract of Japan (2007).
English language Abstract of Japanese Patent Publication No. JP 2007-284387 A, Japanese Patent Office, Patent & Utility Model Gazette DB, Patent Abstract of Japan (2007).
International Search Report of International Application No. PCT/EP2010/004844, European Patent Office, Rijswijk, Netherlands, mailed Oct. 5, 2010.
Office Action mailed Aug. 2, 2012, in U.S. Appl. No. 12/836,696, Andersch, W. et al., filed Jul. 15, 2010.

* cited by examiner

*Primary Examiner* — Shawquia Young
(74) *Attorney, Agent, or Firm* — Sterne, Kessler, Goldstein & Fox P.L.L.C.

(57) ABSTRACT

The present invention constitutes new 3-triazolylphenyl-substituted sulphide derivatives of the formula (I)

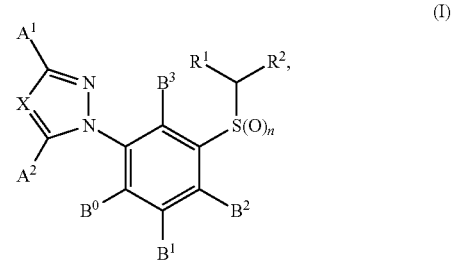

in which $A^1$, $A^2$, $B^0$, $B^1$, $B^2$, $B^3$, X, $R^1$, $R^2$ and n are as defined in the description, to their use as acaricides and insecticides for controlling animal pests, and to processes for preparing them.

26 Claims, No Drawings

3-TRIAZOLYLPHENYL-SUBSTITUTED SULPHIDE DERIVATIVES AS ACARICIDES AND INSECTICIDES

FIELD OF THE INVENTION

The present invention relates to new 3-triazolylphenyl-substituted sulphide derivatives, to their use as acaricides and insecticides for controlling animal pests, and to processes for preparing them.

BACKGROUND OF THE INVENTION

Various substituted phenylheterocyclyl sulphide derivatives and their insecticidal and acaricidal activity have already been described in the literature, in WO 1999/055668, WO 2006/043635, JP2007-284386, JP 2007-284387, JP 2007-284356 and WO 2009/051245.

The active compounds already known from the specifications identified above exhibit disadvantages in their use, possessing either zero or inadequate insecticidal and/or acaricidal activity toward animal pests, in particular at relatively low application rates.

It is an object of the present invention, therefore, to provide corresponding 3-triazolylphenyl-substituted sulphide derivatives which can be used as insecticides and/or acaricides with a satisfactory insecticidal and/or acaricidal activity towards animal pests, particularly at relatively low application rates, with a high selectivity and high compatibility in crop-plant cultures.

SUMMARY OF THE INVENTION

New compounds have now been found of the formula (I)

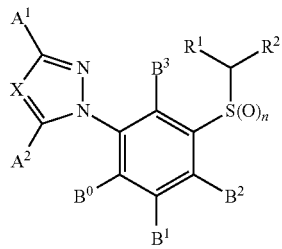

(I)

in which

X is N or C-$A^0$, where $A^0$ is hydrogen, halogen, cyano, alkyl, alkoxy, haloalkyl, haloalkoxy, alkoxyalkyl, alkoxyalkoxy, acyl, haloalkylcarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or R3 and R4, together with the N atom to which they are attached, may form an optionally substituted, saturated or unsaturated, five- to eight-membered ring which is optionally interrupted by heteroatoms, $A^1$ is trifluoromethyl if X is N, or is hydrogen, alkyl, haloalkyl, alkoxyalkyl, acyl, haloalkylcarbonyl, carboxyl or alkoxycarbonyl if X is C-$A_0$, $A^2$ is hydrogen, $B^0$ is hydrogen, amino, halogen, cyano, nitro, alkyl, haloalkyl, alkylthio, haloalkylthio, alkoxy or haloalkoxy, $B^1$, $B^2$ and $B^3$ independently of one another are each hydrogen, halogen, cyano, nitro, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, alkoxycarbonylalkoxy, alkoxyalkoxy, alkylthio, haloalkylthio, alkoxyalkylthio, alkylsulphinyl, haloalkylsulphinyl, alkoxyalkylsulphinyl, alkylsulphonyl, haloalkylsulphonyl, alkoxyalkylsulphonyl, acyl, haloalkylcarbonyl, carboxyl, alkoxycarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted saturated or unsaturated, five- to eight-membered ring which is optionally interrupted by heteroatoms, n is the number 0, 1 or 2, $R^1$ is hydrogen or alkyl, $R^2$ is $CHF_2$, $CF_2Cl$, $CFCl_2$, $CH_2Cl$, $CHCl_2$, $CCl_3$ cyano, ($C_2$-$C_6$)haloalkyl, or is optionally substituted cycloalkyl or cycloalkenyl each of which is interrupted by one or more heteroatoms, or is substituted cycloalkyl or cycloalkenyl, and, if $R^1$ is not hydrogen, $R^2$ may additionally be $CF_3$.

DETAILED DESCRIPTION OF THE INVENTION

Taking account of the definition of X and $A^0$ results in the following structures of the formula (I-A) and (I-B),

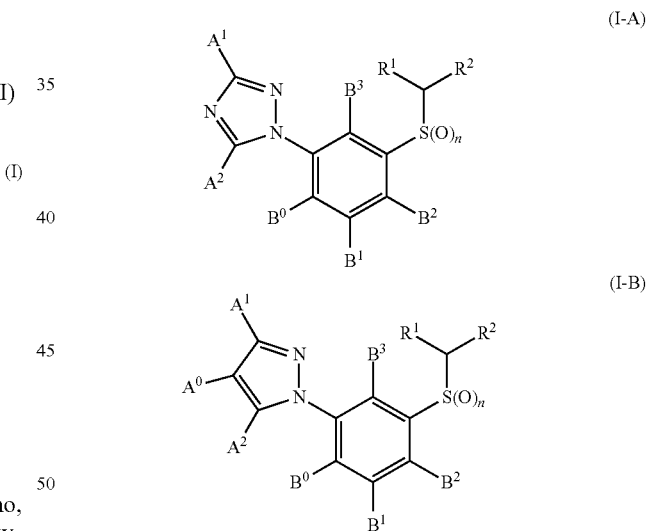

in which $A^1$, in the case of the structure (I-A), is trifluoromethyl, or, in the case of the structure (I-B), is hydrogen, alkyl, haloalkyl, alkoxyalkyl, acyl, haloalkylcarbonyl, carboxyl or alkoxycarbonyl, and $A^2$, $B^0$, $B^1$, $B^2$, $B^3$, $R^1$, $R^2$ and n are defined as indicated above.

The compounds of the formula (I) may possibly exist in different polymorphic forms or as a mixture of different polymorphic forms. Not only the pure polymorphs but also the polymorph mixtures are subject matter of the invention and can be used in accordance with the invention.

The compounds of the formula (I) may comprise diastereomers or enantiomers.

The compounds of the invention are defined in general terms by the formula (I). Preferred substituents and ranges of the radicals given in the formulae referred to above and below are defined
where X preferably is N or C-A⁰, where A⁰ is hydrogen, halogen, cyano, ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)alkoxy-($C_1$-$C_6$)alkyl, ($C_1$-$C_6$)alkoxy-($C_1$-$C_6$)alkoxy, ($C_1$-$C_7$)acyl, ($C_2$-$C_5$)haloalkylcarbonyl or $NR^3R^4$ where $R^3$ and $R^4$ independently of one another are hydrogen, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)alkylthio-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_7$)acyl, ($C_2$-$C_7$)alkoxycarbonyl, or $R^3$ and $R^4$, together with the N atom to which they are attached, may form an optionally ($C_1$-$C_4$)alkyl-, ($C_1$-$C_4$)alkoxy- and/or ($C_1$-$C_4$)haloalkyl-substituted, saturated or unsaturated, five- or six-membered ring which is optionally interrupted by heteroatoms, $A^1$ preferably is trifluoromethyl if X is N (structure I-A), or preferably is hydrogen, ($C_1$-$C_6$)alkyl, ($C_1$-$C_6$)haloalkyl, ($C_1$-$C_3$)alkoxy-($C_1$-$C_6$)alkyl, ($C_1$-$C_7$)acyl, ($C_2$-$C_5$)haloalkylcarbonyl, carboxyl or ($C_2$-$C_7$)alkoxycarbonyl if X is C-A⁰ (structure I-B), $A^2$ preferably is hydrogen, $B^0$ preferably is hydrogen, amino, halogen, cyano, nitro, ($C_1$-$C_6$)alkyl, ($C_1$-$C_6$)haloalkyl, ($C_1$-$C_6$)alkylthio, ($C_1$-$C_6$)haloalkylthio, ($C_1$-$C_6$)alkoxy, ($C_1$-$C_6$)haloalkoxy, $B^1$, $B^2$ and $B^3$ independently of one another preferably are each hydrogen, halogen, cyano, nitro, ($C_1$-$C_6$)alkyl, ($C_1$-$C_6$)haloalkyl, ($C_1$-$C_6$)cyanoalkyl, ($C_1$-$C_6$)hydroxyalkyl, ($C_2$-$C_7$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_2$-$C_5$)alkoxycarbonyl-($C_1$-$C_6$)alkoxy, ($C_1$-$C_3$)alkoxy-($C_1$-$C_6$)alkoxy, ($C_1$-$C_6$)alkylthio, ($C_1$-$C_6$)haloalkylthio, ($C_1$-$C_3$)alkoxy-($C_1$-$C_6$)alkylthio, ($C_1$-$C_6$)alkylsulphinyl, ($C_1$-$C_6$)haloalkylsulphinyl, ($C_1$-$C_3$)alkoxy-($C_1$-$C_6$)alkylsulphinyl, ($C_1$-$C_6$)alkylsulphonyl, ($C_1$-$C_6$)haloalkylsulphonyl, ($C_1$-$C_3$)alkoxy-($C_1$-$C_6$)alkylsulphonyl, ($C_1$-$C_7$)acyl, ($C_2$-$C_5$)haloalkylcarbonyl, carboxyl, ($C_2$-$C_7$)alkoxycarbonyl or $NR^3R^4$, where $R^3$ and $R^4$ independently of one another are hydrogen, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)alkylthio-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_7$)acyl, ($C_2$-$C_7$)alkoxycarbonyl, or $R^3$ and $R^4$, together with the N atom to which they are attached, may form an optionally ($C_1$-$C_4$)alkyl-, ($C_1$-$C_4$)alkoxy-, ($C_1$-$C_4$)haloalkyl-substituted saturated or unsaturated, five- or six-membered ring which is optionally interrupted by heteroatoms, n preferably is the number 0, 1 or 2, $R^1$ preferably is hydrogen or ($C_1$-$C_4$)alkyl, $R^2$ preferably is $CHF_2$, $CF_2Cl$, $CFCl_2$, $CH_2Cl$, $CHCl_2$, $CCl_3$, cyano or ($C_2$-$C_6$)haloalkyl, or is optionally substituted ($C_3$-$C_8$)cycloalkyl or ($C_3$-$C_8$)cycloalkenyl each of which is optionally interrupted by one or more heteroatoms, or is substituted ($C_3$-$C_6$)cycloalkyl or ($C_3$-$C_6$)cycloalkenyl, and, if $R^1$ is other than hydrogen, $R^2$ may additionally be $CF_3$.

The compounds of the invention are defined in general terms by the formula (I). Very preferred substituents and ranges of the radicals given in the formulae referred to above and below are defined where X very preferably is N or C-A⁰, where A⁰ is hydrogen, halogen, cyano, ($C_1$-$C_4$)alkyl, ($C_1$-$C_4$)alkoxy or ($C_1$-$C_4$)haloalkyl, $A^1$ very preferably is trifluoromethyl if X is N (structure I-A), or very preferably is hydrogen, ($C_1$-$C_4$)alkyl, ($C_1$-$C_4$)haloalkyl, ($C_1$-$C_4$)alkoxy-($C_1$-$C_4$)alkyl, ($C_1$-$C_4$)acyl, ($C_2$-$C_4$)haloalkylcarbonyl, carboxyl or ($C_2$-$C_4$)alkoxycarbonyl if X is C-A⁰ (structure I-B), $A^2$ very preferably is hydrogen, $B^0$ very preferably is hydrogen, amino, halogen, cyano, nitro, ($C_1$-$C_4$)alkyl, ($C_1$-$C_4$)haloalkyl, ($C_1$-$C_4$)alkylthio, ($C_1$-$C_4$)haloalkylthio, ($C_1$-$C_4$)alkoxy or ($C_1$-$C_4$)haloalkoxy, $B^1$, $B^2$ and $B^3$ independently of one another very preferably are hydrogen, halogen, cyano, nitro, ($C_1$-$C_4$)alkyl, ($C_1$-$C_4$)haloalkyl, ($C_2$-$C_4$)alkenyl, ($C_1$-$C_4$)alkoxy or ($C_1$-$C_4$)haloalkoxy, n very preferably is the number 0 or 1, $R^1$ very preferably is hydrogen or ($C_1$-$C_2$)alkyl, $R^2$ very preferably is $CHF_2$, $CF_2Cl$, $CFCl_2$, $CH_2Cl$, $CHCl_2$, cyano or ($C_2$-$C_4$)haloalkyl, optionally substituted ($C_3$-$C_6$)cycloalkyl or ($C_3$-$C_6$)cycloalkenyl which is interrupted by one or more heteroatoms, or is substituted ($C_3$-$C_6$)cycloalkyl, and, if $R^1$ is not hydrogen, $R^2$ may additionally be $CF_3$.

The compounds of the invention are defined in general terms by the formula (I). Especially preferred substituents and ranges of the radicals indicated in the formulae refererd to above and below are defined where X especially preferably is N, $A^1$ especially preferably is $CF_3$, $A^2$ especially preferably is hydrogen, $B^0$ especially preferably is hydrogen, methyl, ethyl, fluoro, chloro, methoxy, cyano, $CHF_2$, $CF_3$ or $OCF_3$, $B^1$ especially preferably is hydrogen, $B^2$ especially preferably is hydrogen, methyl, ethyl, fluoro, chloro, methoxy, cyano, $CHF_2$, $CF_3$ or $OCF_3$, $B^3$ especially preferably is hydrogen, n especially preferably is the number 0 or 1, $R^1$ especially preferably is hydrogen, $R^2$ especially preferably is $CHF_2$, $CH_2Cl$, $CHCl_2$, $CCl_3$, $CF_2Cl$, $CFCl_2$, $CF_2CF_3$, $CF_2CHF_2$, $CF_2CF_2Cl$, $CH_2CF_3$, $CH_2CHF_2$ or cyano.

The definitions of radicals, and explanations, that are given above in general or in ranges of preference may be combined arbitrarily with one another, thus including combinations between the respective ranges and ranges of preference. The definitions and explanations apply to the end products and also to the precursors and intermediates accordingly.

Preferred in accordance with the invention are the compounds of the formula (I) in which there is a combination of the definitions given above as being preferred (preferably).

Very preferred in accordance with the invention are the compounds of the formula (I) in which there is a combination of the definitions given above as being very preferable.

Especially preferred in accordance with the invention are the compounds of the formula (I) in which there is a combination of the definitions given above as being especially preferable.

Saturated or unsaturated hydrocarbon radicals such as alkyl, alkanediyl or alkenyl may in each case, both alone and in conjunction with heteroatoms, as in alkoxy, for example, be—where possible—either straight-chain or branched.

Any substituted radicals may, unless indicated otherwise, be substituted one or more times, and the substituents in the case of multiple substitutions may be alike or different.

In the definitions of radicals that are stated as being preferred, halogen (halo) is fluoro, chloro, bromo and iodo, very preferably fluoro, chloro and bromo, and especially preferably fluoro and chloro.

The following compounds of the formula (I-A) are included specifically.

TABLE 1

(I-A)

| $A^1$ | $B^0$ | $B^2$ | $R^2$ | n |
|---|---|---|---|---|
| $CF_3$ | Me | Me | $CHF_2$ | 0 |
| $CF_3$ | Me | Me | $CF_2Cl$ | 0 |
| $CF_3$ | Me | Me | $CFCl_2$ | 0 |
| $CF_3$ | Me | Me | $CF_2CF_3$ | 0 |
| $CF_3$ | Me | Me | $CF_2CHF_2$ | 0 |
| $CF_3$ | Me | Me | $CF_2CF_2Cl$ | 0 |
| $CF_3$ | Me | Me | $CH_2CF_3$ | 0 |
| $CF_3$ | Me | Me | $CH_2CHF_2$ | 0 |
| $CF_3$ | Me | Me | $CHF_2$ | 1 |
| $CF_3$ | Me | Me | $CF_2Cl$ | 1 |
| $CF_3$ | Me | Me | $CFCl_2$ | 1 |
| $CF_3$ | Me | Me | $CF_2CF_3$ | 1 |
| $CF_3$ | Me | Me | $CF_2CHF_2$ | 1 |
| $CF_3$ | Me | Me | $CF_2CF_2Cl$ | 1 |
| $CF_3$ | Me | Me | $CH_2CF_3$ | 1 |
| $CF_3$ | Me | Me | $CH_2CHF_2$ | 1 |

TABLE 2

$A^1$, $R^2$ and n as indicated in Table 1
$B^0$ = H; $B^2$ = CN

TABLE 3

$A^1$, $R^2$ and n as indicated in Table 1
$B^0$ = H; $B^2$ = Me

TABLE 4

$A^1$, $R^2$ and n as indicated in Table 1
$B^0$ = H; $B^2$ = $CHF_2$

TABLE 5

$A^1$, $R^2$ and n as indicated in Table 1
$B^0$ = F; $B^2$ = CN

TABLE 6

$A^1$, $R^2$ and n as indicated in Table 1
$B^0$ = F; $B^2$ = Me

TABLE 7

$A^1$, $R^2$ and n as indicated in Table 1
$B^0$ = F; $B^2$ = $CHF_2$

TABLE 8

$A^1$, $R^2$ and n as indicated in Table 1
$B^0$ = Cl; $B^2$ = CN

TABLE 9

$A^1$, $R^2$ and n as indicated in Table 1
$B^0$ = Cl; $B^2$ = Me

TABLE 10

$A^1$, $R^2$ and n as indicated in Table 1
$B^0$ = Cl; $B^2$ = $CHF_2$

TABLE 11

$A^1$, $R^2$ and n as indicated in Table 1
$B^0$ = Me; $B^2$ = Cl

TABLE 12

$A^1$, $R^2$ and n as indicated in Table 1
$B^0$ = F; $B^2$ = Cl

TABLE 13

$A^1$, $R^2$ and n as indicated in Table 1
$B^0$ = H; $B^2$ = Cl

TABLE 14

$A^1$, $R^2$ and n as indicated in Table 1
$B^0$ = H; $B^2$ = $CF_3$

Preparation Processes

The compounds of the general formula (I) can be prepared using the methods described in application WO 1999/055668. Alternatively to these described methods, the compounds of the formula (I-A) may also be prepared by processes (A) or (A').

Process A
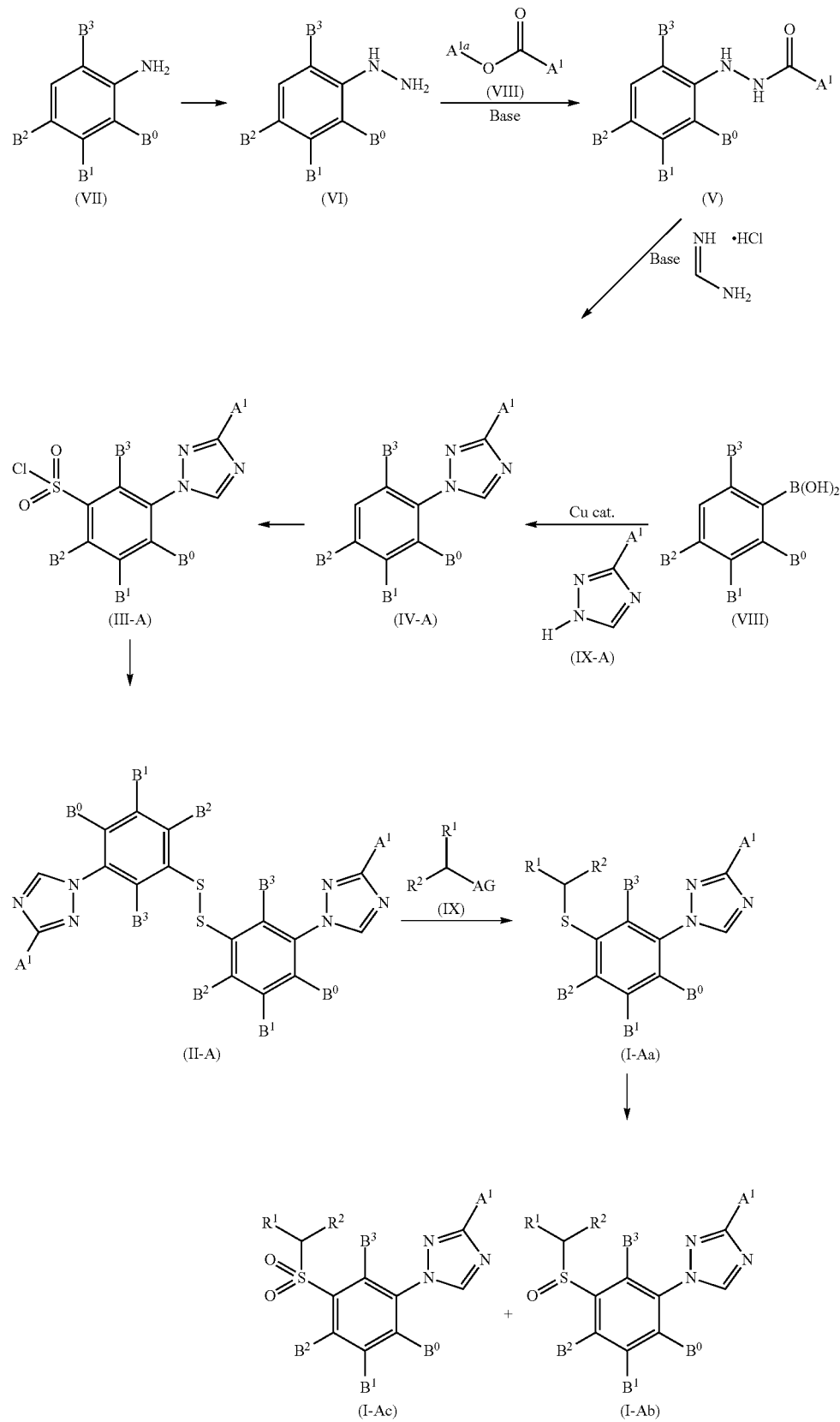

Process A'

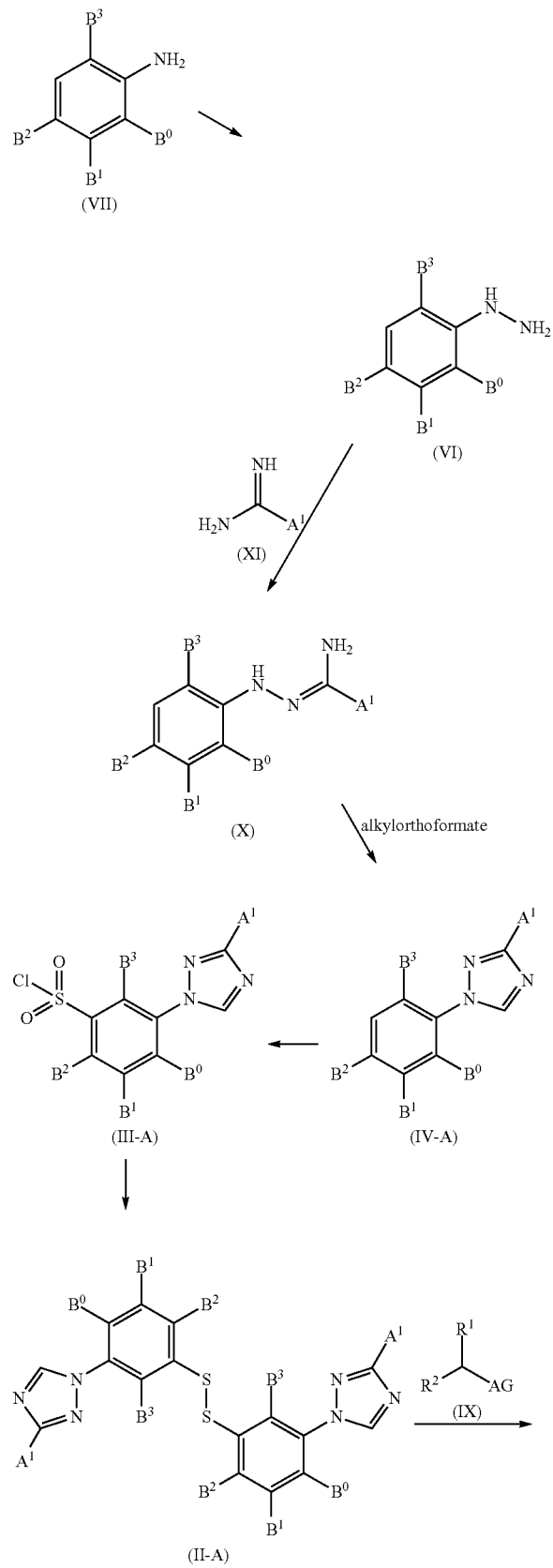

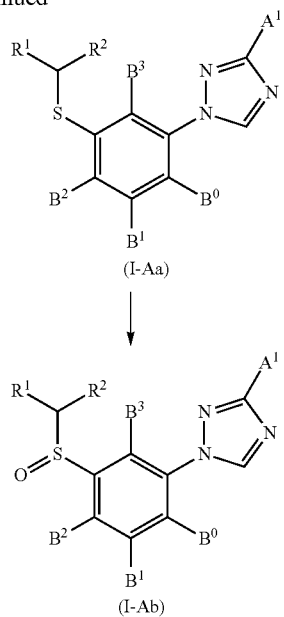

where $A^1$, $B^0$, $B^1$, $B^2$, $B^3$, $R^1$ and $R^2$ are as defined above and $A^{1a}$ is alkyl, preferably $(C_1-C_6)$alkyl.

Anilines of the formula (VII) are either available commercially or can be prepared by known methods. The anilines (VII) are converted with sodium nitrite in the presence of hydrochloric acid into the corresponding diazonium salts and then reduced with tin chloride to give hydrazines of the formula (VI). In the presence of esters (VIII), the hydrazines (VI) are converted into the corresponding hydrazides (V). Hydrazides (V) are reacted with formamidine hydrochloride in the presence of a base, such as sodium hydrogen carbonate, the triazoles of the formula (IV-A) being formed. Alternatively the hydrazines (VI) can be converted into the corresponding amidrazones of the formula (X) in the presence of amidines of the formula (XI) or salts thereof such as, for example, amidinium hydrochlorides or amidinium sulphates. Amidrazones of the formula (X) are reacted with an orthoformate such as, for example, methyl orthoformate or ethyl orthofotinate, forming the triazoles of the formula (IV-A). The triazoles of the formula (IV-A) may also be prepared via copper-catalyzed coupling reaction with the boronic acids of the formula (VIII), and triazoles of the formula (IX-A): application EP1076053B1. The sulphochlorination of the triazoles (IV-A) with chlorosulphonic acid yields the correesponding sulphonyl chlorides (III-A). The sulphonyl chlorides (III-A) can be reduced to give the disulphides (II-A) by methods known from the literature, such as iron in hydrochloric acid, hydrogen iodide or iodides, for example. The reaction of the disulphides with electrophiles of the formula (IX), where AG is a leaving group such as chloro, bromo, tosylate, mesylate or triflate, yields the sulphides (I-Aa). The thioethers are converted into the corresponding sulphoxides (I-Ab) and sulphones (I-Ac) by reaction with oxidizing agents such as, for example, meta-chloroperbenzoic acid.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the *Anoplura (Phthiraptera)*, for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceuthorhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnostema consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix viridana, Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

The present invention accordingly further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

All suitable carriers may in principle be used. Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or POP ethers, acid and/or POP-POE esters, alkylaryl and/or POP-POE ethers, fat- and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

There may possibly be further auxiliaries present in the formulations and the application forms derived from them. Examples of such additives include protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for fomulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations generally comprise between 0.01 and 98% by weight of active compound, preferably between 0.5 and 90%.

The active compounds according to the invention may be used as they are or in their formulations, including a mixture with one or more suitable fungicides, bactericides, acaricides, nematicides, insecticides, microbiologicals, fertilizers, attractants, phytotonics, sterilants, synergists, safeners, semiochemicals and/or plant growth regulators, in order thereby, for example, to broaden the activity spectrum, to prolong the duration of action, to increase the rate of action, to prevent repulsion or to prevent development of resistance. Furthermore, combinations of this kind may improve plant growth, raise tolerance towards abiotic factors such as high or low temperatures, against drought or against increased levels of water and/or soil salt. It is also possible to improve the flowering and fruiting behaviour, the capacity for germination and rooting, to facilitate harvesting and increase yields, to influence ripening, to increase the quality and/or nutritional value of the harvested products, to prolong storage life and/or to improve the manageability of the harvested products. Generally speaking, combining the active compounds of the invention and co-components produces synergistic effects—that is, the activity of the mixture in question is greater than the activity of the individual components. In general it is possible to use the combinations not only in premixes, tank-mixes or ready-made mixes but also in seed applications.

Particularly favourable co-components are, for example, those listed below.

Insecticides/Acaricides/Nematicides

The active compounds identified here by their common name are known and are described in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxy-carboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, such as, for example, pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor.

(4) Nicotinergic acetylcholine receptor agonists, such as, for example, neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), such as, for example, spinosyns, for example spinetoram and spinosad.

(6) Chloride channel activators, such as, for example, avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active compounds with unknown or non-specific mechanisms of action, such as, for example, fumigants, for example methyl bromide and other alkyl halides; or chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, such as, for example, *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, such as, for example, diafenthiuron; or organotin compounds, for example azocyclotin, cyhexatin, fenbutatin oxide; or propargite; tetradifon.

(13) Oxidative phoshorylation decouplers acting by interrupting the H proton gradient, such as, for example, chlorfenapyr and DNOC.

(14) Nicotinergic acetylcholine receptor antagonists, such as, for example, bensultap, cartap (hydrochloride), thiocyclam, and thiosultap (sodium).

(15) Chitin biosynthesis inhibitors, type 0, such as, for example, benzoylureas, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Moulting disruptors, such as, for example, cyromazine.

(18) Ecdysone agonists/disruptors, such as, for example, diacylhydrazines, for example chromafenozide, halofenozide, methoxyfenozide and tebufenozide.

(19) Octopaminergic agonists, such as, for example, amitraz.

(20) Complex-III electron transport inhibitors, such as, for example, hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Derris).

(22) Voltage-dependent sodium channel blockers, for example indoxacarb; metaflumizone.

(23) Inhibitors of acetyl-CoA carboxylase, such as, for example, tetronic acid derivatives, for example spirodiclofen and spiromesifen; or tetramic acid derivatives, for example spirotetramat.

(24) Complex-IV electron transport inhibitors, such as, for example, phosphines, for example aluminium phosphide, calcium phosphide, phosphine, zinc phosphide; or cyanide.

(25) Complex-II electron transport inhibitors, such as, for example, cyenopyrafen.

(28) Ryanodine receptor effectors, such as, for example, diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]

phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

Further active compounds with unknown mechanism of action, such as, for example, azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (1-1582, BioNeem, Votivo) and also the known active compounds below 4-{[(6-bromopyrid-3-yl)methyl](2-fluoroethyl)amino}furan-2(5H)-one (known from WO 2007/115644),
4-{[(6-fluoropyrid-3-yl)methyl](2,2-difluoroethyl)amino}furan-2(5H)-one (known from WO 2007/115644),
4-{[(2-chloro-1,3-thiazol-5-yl)methyl](2-fluoroethyl)amino}furan-2(5H)-one (known from WO 2007/115644),
4-{[(6-chloropyrid-3-yl)methyl](2-fluoroethyl)amino}furan-2(5H)-one (known from WO 2007/115644),
4-{[(6-chloropyrid-3-yl)methyl](2,2-difluoroethyl)amino}furan-2(5H)-one (known from WO 2007/115644),
4-{[(6-chloro-5-fluoropyrid-3-yl)methyl](methyl)amino}furan-2(5H)-one (known from WO 2007/115643),
4-{[(5,6-dichloropyrid-3-yl)methyl](2-fluoroethyl)amino}furan-2(5H)-one (known from WO 2007/115646),
4-{[(6-chloro-5-fluoropyrid-3-yl)methyl](cyclopropyl)amino}furan-2(5H)-one (known from WO 2007/115643),
4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134) and its diastereomers (A) and (B)

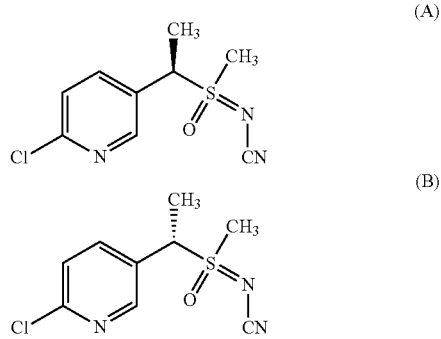

(also known from WO 2007/149134), [(6-trifluoromethylpyridin-3-yl)methyl](methyl)oxido-$\lambda^4$-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635),

[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2006/129714), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407) and N-[1-(2,3-dimethylphenyl)-2-(3,5-dimethylphenyl)ethyl]-4,5-dihydro-1,3-thiazole-2-amine (known from WO2008/104503).

Fungicides (1) Ergosterol biosynthesis inhibitors, such as, for example, aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]-1H-imidazole-1-carbothioate.

(2) Respiration inhibitors (respiratory-chain inhibitors), such as, for example, bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide.

(3) Respiration inhibitors (respiratory-chain inhibitors) on the complex III of the respiratory chain, such as, for example, ametoctradin, amisulbrom, azoxystrobin, cyazofamid, dimoxystrobin, enestroburin, famoxadon, fenamidon, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3- chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]-ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}-oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, such as, for example, benomyl, carbendazim, chlorfenazole, diethofencarb, ethaboxam, fluopicolid, fuberidazole, pencycuron, thiabendazole, thiophanate-methyl, thiophanate, zoxamide, 5-chloro-7-(4-methylpiperidin-1-yl)-6-(2,4,6-trifluorophenyl)-[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multi-site activity, such as, for example, Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, man copper, mancozeb, maneb, metiram, metiram-zinc, oxinecopper, propamidine, propineb, sulphur and sulphur preparations such as, for example, calcium polysulphide, thiram, tolylfluanid, zineb and ziram.

(6) Resistance inductors, such as, for example, acibenzolar-S-methyl, isotianil, probenazole and tiadinil.

(7) Amino acid and protein biosynthesis inhibitors, such as, for example, andoprim, blasticidin-S, cyprodinil, kasugamycin, kasugamycin hydrochloride hydrate, mepanipyrim and pyrimethanil.

(8) ATP production inhibitors, such as, for example, fentin acetate, fentin chloride, fentin hydroxide and silthiofan.

(9) Cell wall synthesis inhibitors, such as, for example, benthiavalicarb, dimethomorph, flumorph, iprovalicarb, mandipropamid, polyoxins, polyoxorim, validamycin A and valifenalate.

(10) Lipid and membrane synthesis inhibitors, such as, for example, biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, such as, for example, carpropamid, diclocymet, fenoxanil, fthalide, pyroquilon and tricyclazole.

(12) Nucleic acid synthesis inhibitors, such as, for example, benalaxyl, benalaxyl M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, such as, for example, chlozolinate, fenpiclonil, fludioxonil, iprodione, procymidon, quinoxyfen and vinclozoline.

(14) Decouplers, such as, for example, binapacryl, dinocap, ferimzone, fluazinam and meptyldinocap.

(15) Further compounds, such as, for example, benthiazole, bethoxazin, capsimycin, carvone, chinomethionat, chlazafenon, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromid, flusulfamide, flutianil, fosetyl-aluminium, fosetyl-calcium, fosetyl-sodium, hexachlorobenzene, irumamycin, methasulphocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and its salts, phenothrin, phosphoric acid and its salts, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and its salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-

(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl(methylidene]amino}oxy)methyl]pyridin-2-yl}carbamate, phenazine-1-carboxylic acid, quinolin-8-ol and quinolin-8-ol sulphate (2:1).

(16) Further compounds, such as, for example, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'43-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide All of the stated co-components of classes (1) to (16) can form salts, where appropriate with suitable bases or acids, provided they are capable of so doing on the basis of their functional groups.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention are active not only against plant pests, hygiene pests and stored-product pests but also in the veterinary field against animal parasites (ecto and endoparasites) such as hard ticks, soft ticks, scab mites, harvest mites, flies (stinging and licking), parasitic fly larvae, lice, hair lice, bird lice and fleas. These parasites include:

from the order of the Anoplurida, for example *Haematopinus* spp., *Linognathus* spp., *Pediculus* spp., *Phtirus* spp., *Solenopotes* spp.

from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

from the order of the Siphonapterida, for example *Pulex* spp., *Ctenocephalides* spp., *Xenopsylla* spp., *Ceratophyllus* spp.

from the order of the Heteropterida, for example *Cimex* spp., *Triatoma* spp., *Rhodnius* spp., *Panstrongylus* spp.

from the order of the Blattarida, for example *Blatta orientalis, Periplaneta americana, Blattela germanica, Supella* spp.

from the subclass of the Acari (Acarina) and the orders of the Meta- and Mesostigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Varroa* spp.

from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods, agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish and what are known as experimental animals such as, for example, hamsters, guinea pigs, rats and mice. By controlling these arthropods it is intended to reduce deaths and improve performance (in the case of meat, milk, wool, hides, eggs, honey and the like) so that more economical and simpler animal keeping is made possible by the use of the active compounds according to the invention.

In the veterinary field and in animal keeping, the active compounds according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When used for livestock, poultry, domestic animals and the like, the active compounds of the formula (I) can be applied as formulations (for example powders, emulsions, flowables) which comprise the active compounds in an amount of from 1 to 80% by weight, either directly or after 100- to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotemies formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

Elucidation of the Processes and Intermediates

The preparation examples and use examples which follow are illustrative but not limitative of the invention.

PREPARATION EXAMPLE 3-(Trifluoromethyl)-1-{12,4-dimethyl-5-[(2,2-difluoroethyl)sulphinyl]phenyl}-1H-1,2,4-triazole Stage 1: 3-(Trifluoromethyl)-1-(2,4-dimethylphenyl)-1H-1,2,4-triazole (IV-A-1)

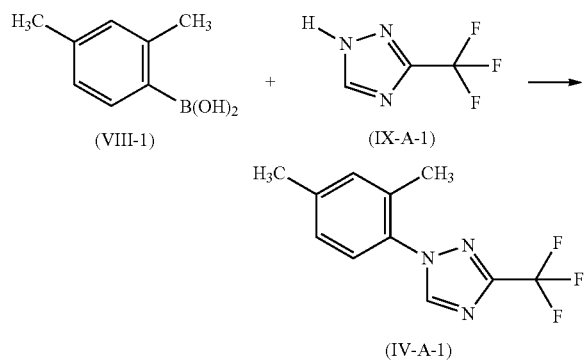

A quantity of 1.32 g of 2,4-dimethylphenylboronic acid and 1.37 g of 3-trifluoromethyl-1,2,4-triazole are heated together with 0.8 g of pyridine and 0.07 g of copper powder in 5 ml of dimethylformamide at 50° C. for 4 hours. Following filtration, the major amount of the DMF is removed by filtration and the product is admixed with dilute 5% strength hydrochloric acid and ethyl acetate. The phases are separated and the organic phase is concentrated on a rotary evaporator. Chromatography ($CH_2Cl_2$) gives 1.27 g of (IV-A-1) (59% of theory)

log P (HCOOH): 3.19

$M^+$: 241

$^1$H NMR ($CDCl_3$): 8.3 (s, 1H), 7.13-7.26 (s+2d, 3H), 2.4 (s, 3H), 2.19 (s, 3H) ppm.

Stage 2: 5-[3-(Trifluoromethyl)-1H-1,2,4-triazol-1-yl]-2,4-dimethylbenzenesulphonyl chloride (III-A-1)

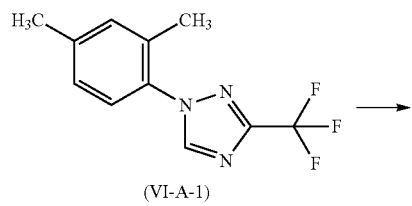

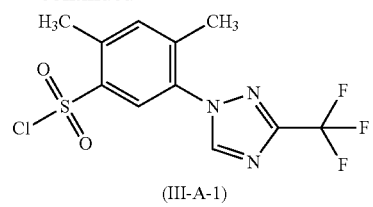

Under a nitrogen atmosphere, 5 g of chlorosulphonic acid are introduced and are admixed at room temperature, in portions, with 3.6 g of 3-(trifluoromethyl)-1-(2,4-dimethylphenyl)-1H-1,2,4-triazole. The exothermic reaction raises the temperature of the mixture to around 45° C. The mixture is subsequently stirred at 70° C. for 3 hours and then cooled, and diluted with 20 ml of methylene chloride. The mixture is added with stirring to ice and then the phases are separated and washed with twice 20 ml of methylene chloride. The combined organic phases are concentrated on a rotary evaporator and then chromatographed ($CH_2Cl_2$). This gives 3.8 g of solid (76% of theory). This solid is reacted further directly.

$M^+$: 339

$^1$H NMR ($CDCl_3$): 8.42 (s, 1H), 8.06 (s, 1H), 7.49 (s, 1H), 2.85 (s, 3H), 2.37 (s, 3H) ppm.

Stage 3: 1,1'-[Disulphanediylbis(4,6-dimethylbenzene-3,1-diyl)]bis[3-(trifluoromethyl)-1H-1,2,4-triazole] (II-A-1)

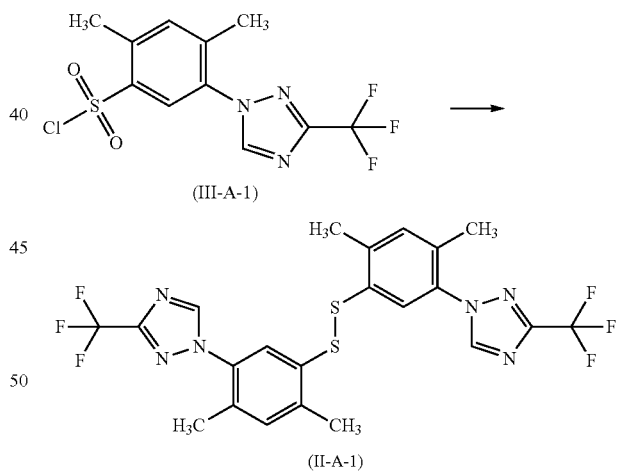

A quantity of 2 g of 5-[3-(trifluoromethyl)-1H-1,2,4-triazol-1-yl]-2,4-dimethylbenzenesulphonyl chloride is dissolved in 25 ml of glacial acetic acid, and 4.6 ml of 32% strength hydrochloric acid are added. The mixture is heated to reflux temperature (120° C.). Then 2.53 g of iron powder are added in portions. Following complete reaction, the major fraction of the glacial acetic acid is removed by distillation, and water and dichloromethane are added. Following phase separation and concentration of the organic phase on a rotary evaporator, 1.3 g (80% of theory) of a beige solid are obtained.

M⁺: 544

¹H NMR (DMSO): 9.19 (s, 2H), 7.63 (s, 2H), 7.36 (s, 2H), 2.4 (s, 6H), 2.14 (s, 6H) ppm.

Stage 4: Preparation of 3-(trifluoromethyl)-1-{2,4-dimethyl-5-[(2,2-difluoroethyl)sulphanyl]phenyl}-1H-1,2,4-triazole (I-A-1)

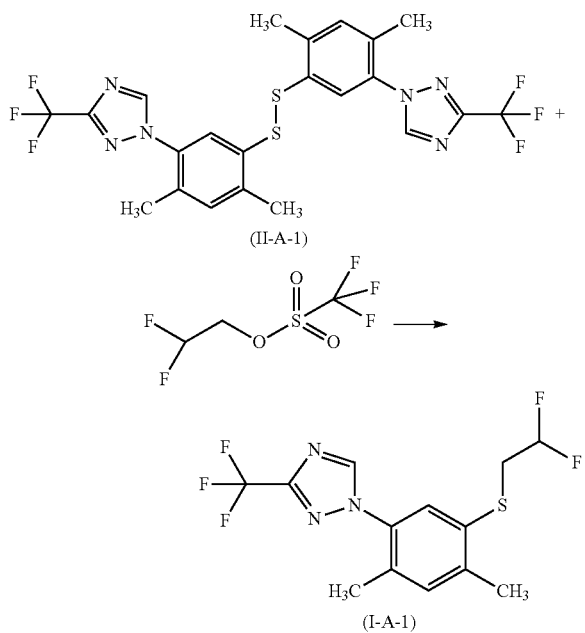

Under nitrogen, 1 g of 1,1'-[disulphanediylbis(4,6-dimethylbenzene-3,1-diyl)]bis[3-(trifluoromethyl)-1H-1,2,4-triazole] is dissolved in 20 ml of dimethylformamide, admixed with 0.96 g of sodium dithionite, 2.04 g of Na₂HPO₄ in 20 ml of water, and stirred at 60° C. for 2 hours, after which 0.76 g of 2,2-difluoroethoxytrifluoromethylsulphonate is added and the mixture is stirred until reaction is complete. The major amount of the dimethylformamide is distilled off under reduced pressure and the residue is stirred with water and methylene chloride. Concentration of the organic phase on a rotary evaporator and chromatographic purification gives 0.45 g of white solid. This corresponds to a yield of 73% of theory.

log P (HCOOH): 3.74
M⁺: 337

¹H NMR (D6-DMSO): 9.10 (s, 1H), 7.63 (s, 1H), 7.36 (s, 1H), 6.13-6.32 (m, 1H), 3.52-3.59 (m, 2H), 2.38 (s, 3H), 2.12 (s, 3H) ppm.

Stage 5: Preparation of 3-(trifluoromethyl)-1-{2,4-dimethyl-5-[(2,2-difluoroethyl)sulphinyl]phenyl}-1H-1,2,4-triazole (I-A-2)

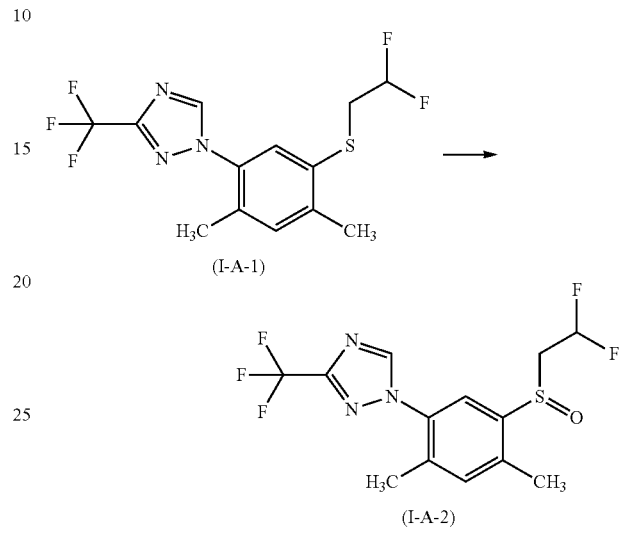

A quantity of 0.3 g of 3-(trifluoromethyl)-1-{2,4-dimethyl-5-[(2,2-difluoroethyl)sulphanyl]phenyl}-1H-1,2,4-triazole is added to 10 ml of trichloromethane and 0.153 g of meta-chloroperbenzoic acid in portions at 0-5° C. and the mixture is stirred at 0-5° C. until conversion is complete. Then 10 ml of water and 3 ml of NaHSO₃ solution are added. The trichloromethane phase is separated off and washed with twice 4 ml of saturated NaHCO₃ solution. Phase separation is followed by concentration on a rotary evaporator, and the residue is chromatographed with CH₂Cl₂/MTBE (19/1). This gives 0.15 g of the desired product (47.7% of theory).

log P (HCOOH): 2.41
M⁺: 353

¹H NMR (D6-DMSO): 9.29 (s, 1H), 7.9 (s, 1H), 7.49 (s, 1H), 6.60-6.31 (m, 1H), 3.50-3.75 (m, 2H), 2.41 (s, 3H), 2.26 (s, 3H) ppm.

The compounds of the formula (I) can be obtained in accordance with the preparation process described above, examples being the following compounds of the formula (I):

| Number | Compound | M⁺ + 1 | logP (HCOOH)[b] | logP (H3PO4)[a] | NMR data (in ppm) |
|---|---|---|---|---|---|
| I-A-1 | | 338 | 3.74 | | 1H NMR (D6-DMSO): 9.19(s, 1H), 7.63 (s, 1H), 7.36 (s, 1H), 6.13-6.32 (m, 1H), 3.52-3.59 (m, 2H), 2.38 (s, 3H), 2.12 (s, 3H) |

-continued

| Number | Compound | M⁺ + 1 | logP (HCOOH)[b] | logP (H3PO4)[a] | NMR data (in ppm) |
|---|---|---|---|---|---|
| I-A-2 | | 354 | 2.41 | | 1H NMR (D6-DMSO): 9.29 (s, 1H), 7.9 (s, 1H), 7.49 (s, 1H), 6.31-6.60 (m, 1H), 3.50-3.75 (m, 2H), 2.41 (s, 3H), 2.26 (s, 3H) |
| I-A-3 | | 388 | 3.98 | | 1H NMR (D6-DMSO): 9.19 (s, 1H), 7.69 (s, 1H), 7.38 (s, 1H), 6.45-6.63 (m, 1H), 3.36-3.82 (m, 2H), 2.42 (s, 3H), 2.13 (s, 3H) |
| I-A-4 | | 406 | 4.49 | | 1H NMR (D6-DMSO): 9.2 (s, 1H), 7.75 (s, 1H), 7.4 (s, 1H), 4.02-4.08 (m, 2H), 2.43 (s, 3H), 2.14 ppm (s, 3H) |
| I-A-5 | | 404 | 2.88 | | 1H NMR (D6-DMSO): 9.3 (s, 1H), 7.97 (s, 1H), 7.51 (s, 1H), 6.47-6.64 (m, 1H), 3.35-3.89 (m, 2H), 2.42 (s, 3H), 2.27 ppm (s, 3H) |
| I-A-6 | | | 3.57 | | 1H NMR (D6-DMSO): 9.31 (s, 1H), 7.91 (d, 1H), 7.55 (d, 1H), 6.09-6.39 (m, 1H), 3.49-3.60 (m, 2H), 2.44 (s, 3H) |
| I-A-7 | | | 2.86 | | 1H NMR (D6-DMSO): 9.26 (S, 1H), 7.80 (s, 1H), 7.48 (s, 1H), 2.92-3.00 (m, 2H), 2.73-2.84 (m, 2H), 2.42 (s, 3H), 2.25 (s, 3H) |

-continued

| Number | Compound | M⁺ + 1 | logP (HCOOH)[b] | logP (H3PO4)[a] | NMR data (in ppm) |
|---|---|---|---|---|---|
| I-A-8 | | | 2.07 | | 1H NMR (D6-DMSO): 9.25 (s, 1H), 7.88 (s, 1H), 7.52 (s, 1H), 4.36-4.40 (d, 1H), 4.64-4.68 (d, 1H), 2.44 (s, 3H), 2.27 (s, 3H) |
| I-A-9 | | | 3.08 | | 1H NMR (D6-DMSO): 9.18 (s, 1H), 7.67 (s, 1H), 7.44 (s, 1H), 4.24 (s, 2H), 2.42 (s, 3H), 2.15 (s, 3H) |
| I-A-10 | | | | 3.29 | 1H NMR (D6-DMSO): 9.31 (m, 1H), 8.01 (s, 1H), 7.51 (s, 1H), 4.11 (t, 2H), 2.44 (s, 3H), 2.28 (s, 3H) |
| I-A-11 | | | 2.17 | | 1H NMR (D6-DMSO): 9.37-9.38 (m, 1H), 8.07 (s, 1H), 7.91-7.92 (m, 1H), 4.75 (d, 1H), 4.45 (d, 1H), 2.48 (s, 3H) |
| I-A-12 | | | 3.12 | | 1H NMR (D6-DMSO): 9.29 (s, 1H), 7.89 (s, 1H), 7.78 (s, 1H), 4.33 (s, 2H), 2.44 (s, 3H) |
| I-A-13 | | | 2.93 | | 1H NMR (D6-DMSO): 9.33 (s, 1H), 7.98 (d, 1H), 7.64 (d, 1H), 4.26 (s, 2H), 2.48 (s, 3H) |
| I-A-14 | | | | 3.4 | 1H NMR (D6-DMSO): 9.39-9.40 (m, 1H), 8.22 (s, 1H), 7.89-7.90 (m, 1H), 4.14-4.22 (m, 2H), 2.48 (s, 3H) |

| Number | Compound | M⁺ + 1 | logP (HCOOH)[b] | logP (H3PO4)[a] | NMR data (in ppm) |
|---|---|---|---|---|---|
| I-A-15 | | | 1.99 | | 1H NMR (D6-DMSO): 9.39 (s, 1H), 8.22 (d, 1H), 7.71 (d, 1H), 4.72 (d, 1H), 4.42 (d, 1H), 2.47 (s, 3H) |
| I-A-16 | | | 3.75 | | 1H NMR (D6-DMSO): 9.25 (s, 1H), 7.86 (s, 1H), 7.67 (s, 1H), 6.10-6.40 (m, 1H), 3.56-3.67 (m, 2H), 2.41 (s, 3H) |
| I-A-17 | | | 4.06 | | 1H NMR (D6-DMSO): 9.26 (s, 1H), 7.91(s, 1H), 7.71 (s, 1H), 6.40-6.68 (m, 1H), 3.83-3.92 (m, 2H), 2.44 (s, 3H) |
| I-A-18 | | | 2.79 | | 1H NMR(D6-DMSO): 9.41 (s, 1H), 8.28 (d, 1H), 7.70 (d, 1H), 6.40-6.70 (m, 1H), 3.74-3.98 (m, 2H), 2.46 (s, 3H) |
| I-A-19 | | | 2.33 | | 1H NMR (D6-DMSO): 9.40 (s, 1H), 8.22 (d, 1H), 7.68 (d, 1H), 6.32-6.61 (m, 1H), 3.46-3.80 (m, 2H), 2.45 (s, 3H) |
| I-A-20 | | | 4.32 | | 1H NMR (D6-DMSO): 9.17-9.18 (m, 1H), 7.51 (s, 1H), 7.36 (s, 1H), 3.18 (t, 2H), 2.58-2.68 (m, 2H), 2.34 (s, 3H), 2.12 (s, 3H) |

-continued

| Number | Compound | M⁺ + 1 | logP (HCOOH)[b] | logP (H3PO4)[a] | NMR data (in ppm) |
|---|---|---|---|---|---|
| I-A-21 | | | 2.54 | | 1H NMR (D6-DMSO): 9.35 (s, 1H), 8.11 (s, 1H), 7.86 (s, 1H), 6.32-6.62 (m, 1H), 3.70-3.83 (m, 1H), 3.48-3.64 (m, 1H), 2.46 (s, 3H) |
| I-A-22 | | | 4.4 | | 1H NMR (D6-DMSO): 9.34 (s, 1H), 8.03-8.05 (d, 1H), 7.58-7.60 (d, 1H), 4.04-4.10 (t, 2H), 2.54 (s, 3H) |
| I-A-23 | | | 3.01 | | 1H NMR (D6-DMSO): 9.37-9.38 (m, 1H), 8.18 (s, 1H), 7.88-7.89 (m, 1H), 6.47-6.65 (m, 1H), 3.92-3.98 (m, 1H), 3.80-3.86 (m, 1H), 2.46 (s, 3H) |
| I-A-24 | | | 3.87 | | 1H NMR (D6-DMSO): 9.31 (s, 1H), 7.97-7.99 (d, 1H), 7.55-7.58 (d, 1H), 6.39-6.68 (tt, 1H), 3.75-3.84 (t, 2H), 2.54 (s, 3H) |
| I-A-25 | | | 3.22 | | 1H NMR (D6-DMSO): 9.42 (s, 1H), 8.33 (d, 1H), 7.70 (d, 1H), 4.15 (t, 2H), 2.47 (s, 3H) |
| I-A-26 | | | 4.57 | | 1H NMR (D6-DMSO): 9.28 (s, 1H), 7.98 (s, 1H), 7.73 (s, 1H), 4.14 (t, 2H), 2.46 (s, 3H) |

Analytical Methods

The log P values reported in the table above and in the preparation examples were determined in accordance with EEC Directive 79/831 Annex V.A8 by HPLC (High Performance Liquid Chromatography) on reversed-phase columns (C 18), with the following methods:

[a] The determination is made in the acid range at pH 2.3 with 0.1% aqueous phosphoric acid and acetonitrile as eluents; linear gradient from 10% acetonitrile to 95% acetonitrile.

[b] The determination is made by LC-MS in the acid range at pH 2.7 with 0.1% aqueous formic acid and acetonitrile (containing 0.1% formic acid) as eluents; linear gradient from 10% acetonitrile to 95% acetonitrile.

Calibration took place with unbranched alkan-2-ones (having 3 to 16 carbon atoms) of known log P values (log P values determined from the retention times by linear interpolation between two successive alkanones).

The lambda-maX values were determined on the basis of the UV spectra from 200 nm to 400 nm in the maxima of the chromatographic signals.

The MH+ signals were determined using an Agilent MSD system with ESI and positive or negative ionization.

The NMR spectra were determined using a Bruker Avance 400, equipped with a flow sample head (60 μl volume). Solvents used were $d_6$-DMSO or $CD_3CN$, with tetramethylsilane (0.00 ppm) used as a reference. The measurement temperature is 303K when using $d_6$-DMSO as solvent, and 298K when using $CD_3CN$ as solvent.

In isolated cases, the samples were determined using a Bruker Avance II 600 or III 600.

The splitting of the signals was described as follows: s (singlet), d (doublet), t (triplet), q (quartet), quin (quintet), m (multiplet).

Use Examples

Example 1

*Boophilus Microplus* (Dip)

Solvent: Dimethyl Sulphoxide

A quantity of 10 mg of active compound is dissolved in 0.5 ml of dimethyl sulphoxide. To prepare a suitable formulation, the active compound solution is diluted with water to the particular desired concentration.

This active compound preparation is pipetted into tubes. A quantity of 8-10 ticks is transferred into a further tube with holes. The tube is immersed in the active compound preparation, with all of the ticks being fully wetted. After the liquid has run off, the ticks are transferred to filter discs in plastic dishes and are kept in a conditioned room. The effect is monitored after 7 days on the basis of deposition of fertile eggs. Eggs whose fertility is not externally visible are stored in glass tubes until the larvae hatch, in a controlled-climate box. An activity of 100% means that none of the ticks has laid fertile eggs.

In this test the following compounds from the preparation examples, for example, exhibit an activity of 90% for an application rate of 100 ppm: I-A-3, I-A-4.

Example 2

*Boophilus Microplus* Test (BOOPMI Injection)

Solvent: Dimethyl Sulphoxide

An appropriate preparation of active compound is prepared by mixing 10 mg of active compound with 0.5 ml of solvent and diluting the concentrate with solvent to the desired concentration. The solution of active compound is injected into the abdomen (*Boophilus microplus*) and the animals are transferred into dishes and kept in a controlled atmosphere. The activity is assessed on the basis of deposition of fertile eggs.

After 7 days, the effect in % is determined. Here, 100% means that none of the ticks has laid fertile eggs.

In this test the following compounds from the preparation examples, for example, exhibit an activity of 100% for an application rate of 20 μg/animal: I-A-1, I-A-2, I-A-3, I-A-4, I-A-5

Example 3

Phaedon Test (PHAECO Spray Treatment)

Solvents: 78.0 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvent and emulsifier and diluting the concentrate with emulsifier-containing water to the desired concentration. Leaf discs of Chinese cabbage (*Brassica pekinensis*) are sprayed with a preparation of active compound at the desired concentration and, after they have dried, are populated with larvae of the mustard beetle (*Phaedon cochleariae*).

After the desired time, the effect in % is determined. Here, 100% means that all of the beetle larvae have been killed; 0% means that no beetle larvae have been killed.

In this test the following compounds from the preparation examples, for example, show an effect of 100% for an application rate of 500 g/ha: I-A-6, I-A-14, I-A-16, I-A-17, I-A-18, I-A-19, I-A-23, I-A-24, I-A-25

Example 4

Myzus Test (MYZUPE Spray Treatment)

Solvent: 78 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvent and emulsifier and diluting the concentrate with emulsifier-containing water to the desired concentration. Leaf discs of Chinese cabbage (*Brassica pekinensis*) infested by all stages of the green peach aphid (Myzus persicae) are sprayed with a preparation of active compound at the desired concentration.

After 6 days, the effect in % is determined. Here, 100% means that all of the aphids have been killed; 0% means that no aphids have been killed.

In this test the following compound from the preparation examples, for example, exhibits an activity of 90% for an application rate of 500 g/ha: I-A-5

In this test the following compound from the preparation examples, for example, exhibits an activity of 100% for an application rate of 500 g/ha: I-A-20

Example 5

Tetranychus Test; OP Resistant (TETRUR Spray Treatment)

Solvents: 78.0 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvent and emulsifier and diluting the concentrate with emulsifier-containing water to the desired concentration. Leaf discs of bean (*Phaseolus vulgaris*) infested by all stages of the greenhouse red spidermite (*Tetranychus urticae*) are sprayed with a preparation of active compound at the desired concentration.

After 6 days, the effect in % is determined. Here, 100% means that all of the mites have been killed; 0% means that no mites have been killed.

In this test the following compounds from the preparation examples, for example, exhibit an effect of 90% for an application rate of 100 g/ha: I-A-7, I-A-26

In this test the following compounds from the preparation examples, for example, exhibit an effect of 100% for an application rate of 100 g/ha: I-A-1, I-A-2, I-A-4, I-A-6, I-A-9, I-A-16, I-A-17, I-A-18, I-A-19, I-A-20, I-A-22, I-A-24, I-A-25

In this test the following compounds from the preparation examples, for example, exhibit and effect of 100% for an application rate of 500 g/ha:
I-A-3, I-A-4, I-A-5, I-A-8, I-A-10, I-A-11, I-A-12, I-A-13, I-A-14, I-A-15, I-A-21, I-A-23

Example 6

*Meloidogyne incognita* Test (MELGIN)

Solvents: 80.0 parts by weight of acetone

An appropriate preparation of active compound is prepared by mixing 1 part by weight of active compound with the stated amounts of solvent and emulsifier and diluting the concentrate with water to the desired concentration. Pots are filled with sand, solution of active compound, meloidogyne incognita egg/larvae suspension, and lettuce seeds. The lettuce seeds germinate and the plants develop. On the roots, the galls develop. After 14 days, the nematicidal effect is determined from the gall formation, in %. Here, 100% means that no galls were found; 0% means that the number of galls on the treated plants corresponds to that for the untreated control.

In this test the following compound from the preparation examples, for example, shows an effect of 90% for an application rate of 20 ppm: I-A-11

Example 7

Tetranychus Test; OP Resistant (TETRUR Spray Treatment)

Solvents: 78.0 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvent and emulsifier and diluting the concentrate with emulsifier-containing water to the desired concentration.

Leaf discs of bean (*Phaseolus vulgaris*) infested by all stages of the greenhouse red spidermite (*Tetranychus urticae*) are sprayed with a preparation of active compound at the desired concentration.

After the desired time, the effect in % is determined. Here, 100% means that all of the mites have been killed; 0% means that no mites have been killed.

In this test the following compounds from the preparation examples, for example, exhibit an activity superior to the prior art:
see table

| Substance | Structure | Object | Concentration | % effect after application |
|---|---|---|---|---|
| VI-297 known from W/O 1999/055668 | 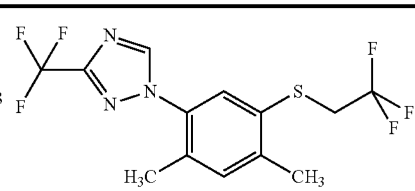 | TETRUR TETRUR | 20 g/ha 4 g/ha | 70 6 d 0 6 d |
| I-A-1 in accordance with the invention | 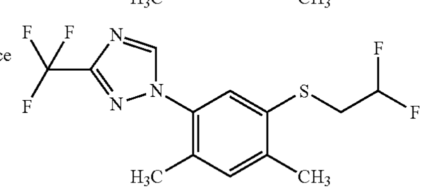 | TETRUR TETRUR | 20 g/ha 4 g/ha | 100 6 d 100 6 d |

The invention claimed is:
1. A 3-Triazolylphenyl-substituted sulphide of formula (I)

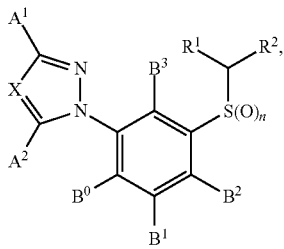

wherein:
X is N or C-$A^0$, where $A^0$ is hydrogen, halogen, cyano, alkyl, alkoxy, haloalkyl, haloalkoxy, alkoxyalkyl, alkoxyalkoxy, acyl, haloalkylcarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted, saturated or unsaturated, five- to eight-membered ring which is optionally interrupted by heteroatoms,
$A^1$ is trifluoromethyl if X is N,
or is hydrogen, alkyl, haloalkyl, alkoxyalkyl, acyl, haloalkylcarbonyl, carboxyl or alkoxycarbonyl if X is C-$A^0$,
$A^2$ is hydrogen,
$B^0$ is hydrogen, amino, halogen, cyano, nitro, alkyl, haloalkyl, alkylthio, haloalkylthio, alkoxy or haloalkoxy,
$B^1$, $B^2$ and $B^3$ independently of one another are each hydrogen, halogen, cyano, nitro, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, alkoxycarbonylalkoxy, alkoxyalkoxy, alkylthio, haloalkylthio, alkoxyalkylthio, alkylsulphinyl, halo alkylsulphinyl, alkoxyalkylsulphinyl, alkylsulphonyl, haloalkylsulphonyl, alkoxyalkylsulphonyl, acyl, haloalkylcarbonyl, carboxyl, alkoxycarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted saturated or unsaturated, five- to eight-membered ring which is optionally interrupted by heteroatoms,
n is the number 0, 1 or 2,
$R^1$ is hydrogen or alkyl,
$R^2$ is $CHF_2$, $CF_2Cl$, $CFCl_2$, $CH_2Cl$, $CHCl_2$, $CCl_3$, cyano, $(C_2-C_6)$haloalkyl, or is optionally substituted cycloalkyl or cycloalkenyl each of which is interrupted by one or more heteroatoms, or is substituted cycloalkyl or cycloalkenyl, and, if $R^1$ is not hydrogen, $R^2$ may additionally be $CF_3$.

2. The 3-Triazolylphenyl-substituted sulphide according to claim 1, where
X is N or C-$A^0$, where $A^0$ is hydrogen, halogen, cyano, $(C_1-C_6)$alkyl, $(C_1-C_6)$alkoxy, $(C_1-C_6)$haloalkyl, $(C_1-C_6)$haloalkoxy, $(C_1-C_6)$alkoxy-$(C_1-C_6)$alkyl, $(C_1-C_6)$alkoxy-$(C_1-C_6)$alkoxy, $(C_1-C_7)$acyl, $(C_2-C_5)$haloalkylcarbonyl or $NR^3R^4$ where $R^3$ and $R^4$ independently of one another are hydrogen, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$alkylthio-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_7)$acyl, $(C_2-C_7)$alkoxycarbonyl, or $R^3$ and $R^4$, together with the N atom to which they are attached, may form an optionally $(C_1-C_4)$alkyl-, $(C_1-C_4)$alkoxy- and/or $(C_1-C_4)$haloalkyl-substituted, saturated or unsaturated, five- or six-membered ring which is optionally interrupted by heteroatoms,
$A^1$ is trifluoromethyl if X is N,
or is hydrogen, $(C_1-C_6)$alkyl, $(C_1-C_6)$haloalkyl, $(C_1-C_3)$alkoxy-$(C_1-C_6)$alkyl, $(C_1-C_7)$acyl, $(C_2-C_5)$haloalkylcarbonyl, carboxyl or $(C_2-C_7)$alkoxycarbonyl if X is C-$A^0$,
$B^0$ is hydrogen, amino, halogen, cyano, nitro, $(C_1-C_6)$alkyl, $(C_1-C_6)$haloalkyl, $(C_1-C_6)$alkylthio, $(C_1-C_6)$haloalkylthio, $(C_1-C_6)$alkoxy, $(C_1-C_6)$haloalkoxy,
$B^1$, $B^2$ and $B^3$ independently of one another are each hydrogen, halogen, cyano, nitro, $(C_1-C_6)$alkyl, $(C_1-C_6)$haloalkyl, $(C_1-C_6)$cyanoalkyl, $(C_1-C_6)$hydroxyalkyl, $(C_2-C_7)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_2-C_5)$alkoxycarbonyl-$(C_1-C_6)$alkoxy, $(C_1-C_{13})$alkoxy-$(C_1-C_6)$alkoxy, $(C_1-C_6)$alkylthio, $(C_1-C_6)$haloalkylthio, $(C_1-C_3)$alkoxy-$(C_1-C_6)$alkylthio, $(C_1-C_6)$alkylsulphinyl, $(C_1-C_6)$haloalkylsulphinyl, $(C_1-C_3)$alkoxy-$(C_1-C_6)$alkylsulphinyl, $(C_1-C_6)$alkylsulphonyl, $(C_1-C_6)$haloalkylsulphonyl, $(C_1-C_3)$alkoxy-$(C_1-C_6)$alkylsulphonyl, $(C_1-C_7)$acyl, $(C_2-C_5)$haloalkylcarbonyl, carboxyl, $(C_2-C_7)$alkoxycarbonyl or $NR^3R^4$, where $R^3$ and $R^4$ independently of one another are hydrogen, $(C_1-C_1)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$alkylthio-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_7)$acyl, $(C_1-C_7)$alkoxycarbonyl, or $R^3$ and $R^4$, together with the N atom to which they are attached, may form an optionally $(C_1-C_4)$alkyl-, $(C_1-C_4)$alkoxy-, $(C_1-C_4)$haloalkyl-substituted saturated or unsaturated, five- or six-membered ring which is optionally interrupted by heteroatoms,
n is the number 0, 1 or 2,
$R^1$ is hydrogen or $(C_1-C_4)$alkyl,
$R^2$ is $CHF_2$, $CF_2Cl$, $CFCl_2$, cyano or $(C_2-C_6)$haloalkyl, or is optionally substituted $(C_3-C_8)$cycloalkyl or $(C_3-C_8)$cycloalkenyl each of which is interrupted by one or more heteroatoms, or is substituted $(C_3-C_6)$cycloalkyl or $(C_3-C_6)$cycloalkenyl, and, if $R^1$ is other than hydrogen, $R^2$ may additionally be $CF_3$.

3. The 3-Triazolylphenyl-substituted sulphide according to claim 1, where
X is N or C-$A^0$, where $A^0$ is hydrogen, halogen, cyano, $(C_1-C_4)$alkyl, $(C_1-C_4)$alkoxy or $(C_1-C_4)$haloalkyl,
$A^1$ is trifluoromethyl if X is N, or is hydrogen, $(C_1-C_4)$alkyl, $(C_1-C_4)$haloalkyl, $(C_1-C_4)$alkoxy-$(C_1-C_4)$alkyl, $(C_1-C_4)$acyl, $(C_2-C_4)$haloalkylcarbonyl, carboxyl or $(C_2-C_4)$alkoxycarbonyl if X is C-$A^0$, $A^2$ is hydrogen, $B^0$ is hydrogen, amino, halogen, cyano, nitro, $(C_1-C_4)$alkyl, $(C_1-C_4)$haloalkyl, $(C_1-C_4)$alkylthio, $(C_1-C_4)$haloalkylthio, $(C_1-C_4)$alkoxy or $(C_1-C_4)$haloalkoxy, $B^1$, $B^2$ and $B^3$ independently of one another are hydrogen, halogen, cyano, nitro, $(C_1-C_4)$alkyl, $(C_1-C_4)$haloalkyl, $(C_2-C_4)$alkenyl, $(C_1-C_4)$alkoxy or $(C_1-C_4)$haloalkoxy, n is the number 0 or 1, $R^1$ is hydrogen or $(C_1-C_2)$alkyl, $R^2$ is $CHF_2$, $CF_2Cl$, $CFCl_2$, cyano or $(C_2-C_4)$haloalkyl, or is optionally substituted $(C_3-C_6)$cycloalkyl or $(C_3-C_6)$cycloalkenyl each of which is interrupted by one or more heteroatoms, or is substituted $(C_3-C_6)$cycloalkyl, and, if $R^1$ is not hydrogen, $R^2$ may additionally be $CF_3$.

4. The 3-Triazolylphenyl-substituted sulphide of formula I-A according to claim 1

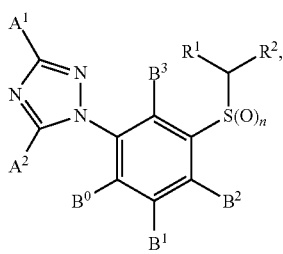

(I-A)

in which $A^1$ is trifluoromethyl and $A^2$ is hydrogen, $B^0$ is hydrogen, amino, halogen, cyano, nitro, alkyl, haloalkyl, alkylthio, haloalkylthio, alkoxy or haloalkoxy, $B^1$, $B^2$ and $B^3$ independently of one another are each hydrogen, halogen, cyano, nitro, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, alkoxycarbonylalkoxy, alkoxyalkoxy, alkylthio, haloalkylthio, alkoxyalkylthio, alkylsulphinyl, haloalkylsulphinyl, alkoxyalkylsulphinyl, alkylsulphonyl, haloalkylsulphonyl, alkoxyalkylsulphonyl, acyl, haloalkylcarbonyl, carboxyl, alkoxycarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted saturated or unsaturated, five- to eight-membered ring which is optionally interrupted by heteroatoms, n is the number 0, 1 or 2, $R^1$ is hydrogen or alkyl, $R^2$ is $CHF_2$, $CF_2Cl$, $CFCl_2$, $CH_2Cl$, $CHCl_2$, $CCl_3$, cyano, $(C_2-C_6)$haloalkyl, or is optionally substituted cycloalkyl or cycloalkenyl each of which is interrupted by one or more heteroatoms, or is substituted cycloalkyl or cycloalkenyl, and, if $R^1$ is not hydrogen, $R^2$ may additionally be $CF_3$.

5. The 3-Triazolylphenyl-substituted sulphide of formula I-B according to claim 1

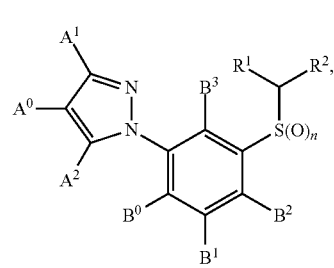

(I-B)

in which $A^0$ is hydrogen, halogen, cyano, alkyl, alkoxy, haloalkyl, haloalkoxy, alkoxyalkyl, alkoxyalkoxy, acyl, haloalkylcarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted, saturated or unsaturated, five- to eight-membered ring which is optionally interrupted by heteroatoms, $A^1$ is hydrogen, alkyl, haloalkyl, alkoxyalkyl, acyl, haloalkylcarbonyl, carboxyl or alkoxycarbonyl and $A^2$ is hydrogen, $B^0$ is hydrogen, amino, halogen, cyano, nitro, alkyl, haloalkyl, alkylthio, haloalkylthio, alkoxy or haloalkoxy, $B^1$, $B^2$ and $B^3$ independently of one another are each hydrogen, halogen, cyano, nitro, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, alkoxycarbonylalkoxy, alkoxyalkoxy, alkylthio, haloalkylthio, alkoxyalkylthio, alkylsulphinyl, haloalkylsulphinyl, alkoxyalkylsulphinyl, alkylsulphonyl, haloalkylsulphonyl, alkoxyalkylsulphonyl, acyl, haloalkylcarbonyl, carboxyl, alkoxycarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted saturated or unsaturated, five- to eight-membered ring which is optionally interrupted by heteroatoms, n is the number 0, 1 or 2, $R^1$ is hydrogen or alkyl, $R^2$ is $CHF_2$, $CF_2Cl$, $CFCl_2$, $CH_2Cl$, $CHCl_2$, $CCl_3$, cyano, $(C_2-C_6)$haloalkyl, or is optionally substituted cycloalkyl or cycloalkenyl each of which is interrupted by one or more heteroatoms, or is substituted cycloalkyl or cycloalkenyl, and, if $R^1$ is not hydrogen, $R^2$ may additionally be $CF_3$.

6. A process for preparing the 3-Triazolylphenyl-substituted sulphide of formula (I-A) according to claim 4, comprising (A) (i) reacting an aniline of formula (VII)

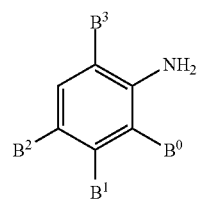
(VII)

with sodium nitrite to provide a diazonium salt; and
(ii) reducing the diazonium salt to give a hydrazine of formula (VI)

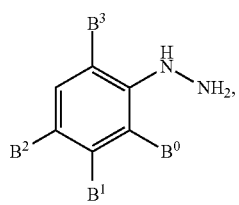
(VI)

(B) reacting the hydrazine of formula (VI) with an ester of formula (VIII)

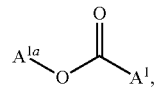
(VIII)

where $A^{1a}$ is alkyl,
to give a hydrazide of formula (V)

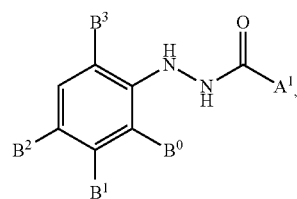
(V)

(C) reacting the hydrazide of formula (V) with formamidine hydrochloride in the presence of a base to give a triazole of formula (IV-A)

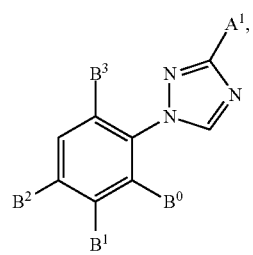
(IV-A)

(D) sulphochlorinating the triazole of formula (IV-A) to give a sulphonyl chloride of formula (III-A)

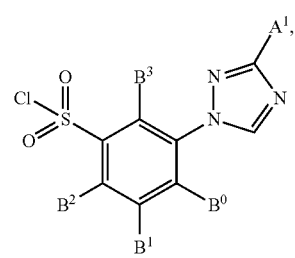
(III-A)

(E) reducing the sulphonyl chloride of formula (III-A) to a disulphide of formula (II-A)

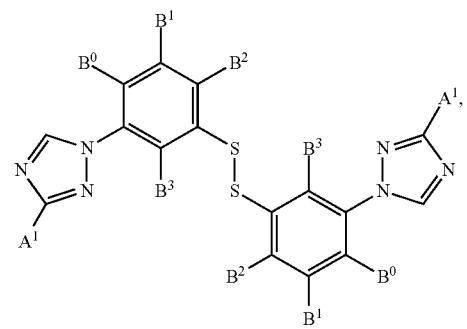
(II-A)

(F) reacting the disulphide of formula (II-A) with an electrophile of formula (IX)

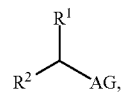
(IX)

where AG is a leaving group,
to give a sulphide of formula (I-Aa)

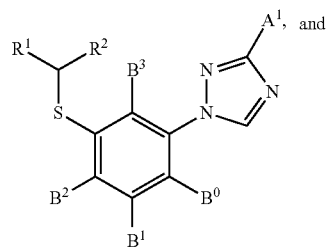
(I-Aa) and (G) reacting the sulphide of formula (I-Aa) with an oxidizing agent to give a sulphoxide of formula (I-Ab)

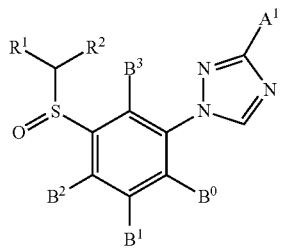
(I-Ab)

and a sulphone of formula (I-Ac)

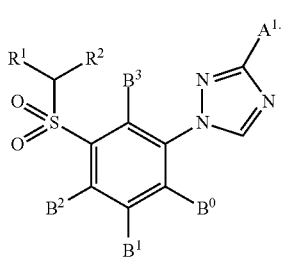
(I-Ac)

7. The process according to claim 6, wherein the triazole of formula (IV-A) is prepared by reacting a boronic acid of formula (VIII)

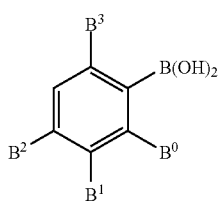
(VIII)

with a triazole of formula (IX-A)

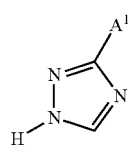
(IX-A)

and with a copper catalyst.

8. The process according to claim 6, wherein the triazole of formula (IV-A) is prepared by reacting a hydrazine of formula (VI)

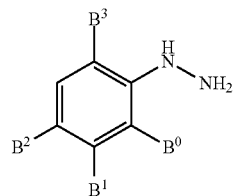
(VI)

with an amidine of formula (XI) or a salt thereof

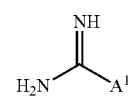
(XI)

to give an amidrazone of formula (X)

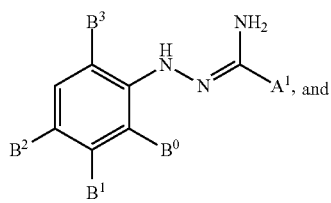
(X)

reacting the amidrazone of formula (X) with an orthoformate.

9. An active compound composition comprising the at least one 3-Triazolylphenyl-substituted sulphide, according to claim 1, of formula (I), or formula (I-A), or formula (I-B); and at least one other active insecticidal, acaricidal or nematicidal compound selected from the group consisting of
(1) Acetylcholinesterase (AChE) inhibitors;
(2) GABA-gated chloride channel antagonists;
(3) Sodium channel modulators;
(4) Nicotinergic acetylcholine receptor agonists;
(5) Allosteric acetylcholine receptor modulators;
(6) Chloride channel activators;
(7) Juvenile hormone analogues;
(8) Active compounds with unknown or non-specific mechanisms of action selected from the group consisting of fumigants, chloropicrin, sulphuryl fluoride, borax and tartar emetic;
(9) Selective antifeedants;
(10) Mite growth inhibitors;
(11) Microbial disruptors of the insect gut membrane;
(12) Oxidative phosphorylation inhibitors;
(13) Oxidative phoshorylation decouplers acting by interrupting a H proton gradient;
(14) Nicotinergic acetylcholine receptor antagonists;
(15) Chitin biosynthesis inhibitors, type 0;
(16) Chitin biosynthesis inhibitors, type 1;
(17) Moulting disruptors;
(18) Ecdysone agonists/disruptors;
(19) Octopaminergic agonists;
(20) Complex-III electron transport inhibitors;
(21) Complex-I electron transport inhibitors;
(22) Voltage-dependent sodium channel blockers;
(23) Inhibitors of acetyl-CoA carboxylase;
(24) Complex-IV electron transport inhibitors;

(25) Complex-II electron transport inhibitors;
(26) Ryanodine receptor effectors;
(27) Further active compounds with unknown mechanism of action selected from the group consisting of azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl, pyrifluquinazon, products based on *Bacillus firmus*, 4-{[(6-bromopyrid-3-yl)methyl](2-fluoroethyl)amino}furan-2(5H)-one, 4-{[(6-fluoropyrid-3-yl)methyl](2,2-difluoroethyl) amino}furan-2(5H)-one, 4-{[(2-chloro-1,3-thiazol-5-yl)methyl](2-fluoroethyl)amino}furan-2(5H)-one, 4-{[(6-chloropyrid-3-yl)methyl](2-fluoroethyl) amino}furan-2(5H)-one, 4-{[(6-chloropyrid-3-yl)methyl](2,2-difluoroethyl)amino}furan-2(5H)-one, 4-{[(6-chloro-5-fluoropyrid-3-yl)methyl](methyl) amino}furan-2(5H)-one, 4-{[(5,6-dichloropyrid-3-yl)methyl](2-fluoroethyl)amino}furan-2(5H)-one, 4-{[(6-chloro-5-fluoropyrid-3-yl)methyl](cyclopropyl) amino}furan-2(5H)-one, 4-{[(6-chloropyrid-3-yl)methyl](cyclopropyl)amino}furan-2(5H)-one, 4-{[(6-chloropyrid-3-yl)methyl](methyl)amino}furan-2(5H)-one, [(6-chloropyridin-3-yl)methyl](methyl)oxido-$\lambda^4$-sulphanylidenecyanamide, [1-(6-chloropyridin-3-yl) ethyl](methyl)oxido-$\lambda^4$-sulphanylidenecyanamide and its diastereomers (A) and (B)

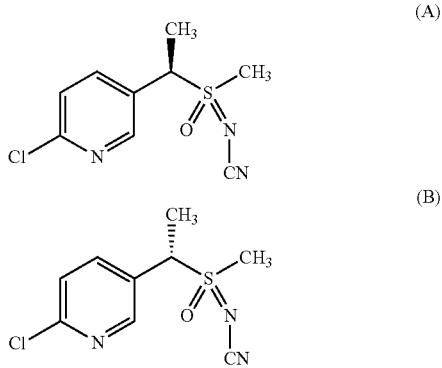

(A)

(B)

[(6-trifluoromethylpyridin-3-yl)methyl](methyl)oxido-$\lambda^4$-sulphanylidenecyanamide, sulfoxaflor,
11-(4-chloro-2,6-dimethylphenyl)-12-hydroxy-1,4-dioxa-9-azadispiro[4.2.4.2]tetradec-11-en-10-one, 3-(4'-fluoro-2,4-dimethylbiphenyl-3-yl)-4-hydroxy-8-oxa-1-azaspiro[4.5]dec-3-en-2-one,
1-[2-fluoro-4-methyl-5-[(2,2,2-trifluoroethyl)sulphinyl] phenyl]-3-(trifluoromethyl)-1H-1,2,4-triazole-5-amine,
[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate,
2-cyano-3-(difluoromethoxy)-N,N-dimethylbenzenesulphonamide,
2-cyano-3-(difluoromethoxy)-N-methylbenzenesulphonamide, 2-cyano-3-(difluoromethoxy)-N-ethylbenzenesulphonamide, 4-(difluoromethoxy)-N-ethyl-N-methyl-1,2-benzothiazole-3-amine 1,1-dioxide and
N-[1-(2,3-dimethylphenyl)-2-(3,5-dimethylphenyl) ethyl]-4,5-dihydro-1,3-thiazole-2-amine, and/or at least one further active fungicidal compound selected from the group consisting of
(28) Ergosterol biosynthesis inhibitors;
(29) Respiration inhibitors;
(30) Respiration inhibitors on complex III of a respiratory chain;
(31) Mitosis and cell division inhibitors;
(32) Compounds with multi-site activity;
(33) Resistance inductors;
(34) Amino acid and protein biosynthesis inhibitors;
(35) ATP production inhibitors;
(36) Cell wall synthesis inhibitors;
(37) Lipid and membrane synthesis inhibitors;
(38) Melanin biosynthesis inhibitors;
(39) Nucleic acid synthesis inhibitors;
(40) Signal transduction inhibitors;
(41) Decouplers;
(42) Further compounds selected from the group consising of benthiazole, bethoxazin, capsimycin, carvone, chinomethionat, chlazafenon, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromid, flusulfamide, flutianil, fosetyl-aluminium, fosetyl-calcium, fosetyl-sodium, hexachlorobenzene, irumamycin, methasulphocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and a salt thereof, phenothrin, phosphoric acid and a salt thereof, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl] piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and its salts, 3,4,5-trichloropyridine-2,6-dicarbonitrile, 3-[5-(4-chlorophenyl)-2,3-dimethyl-1,2-oxazolidin-3-yl] pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-methyl-6-octyl[1,2,4]triazolo[1,5-a]pyrimidin-7-amine, ethyl (2Z)-3-amino-2-cyano-3- phenylprop-2-enoate, N-(4-chlorobenzyl)-3-[3-methoxy-4-(prop-2-yn-1-yloxy)phenyl]propanamide, N-[(4-chlorophenyl)cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinoline-8-ol, quinoline-8-ol sulphate, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide.

10. A composition comprising the at least one 3-Triazolylphenyl-substituted sulphide, according to claim 1, of formula (I), or formula (I-A), or formula (I-B); and at least one penetrant.

11. A disulphide of formula (II-A)

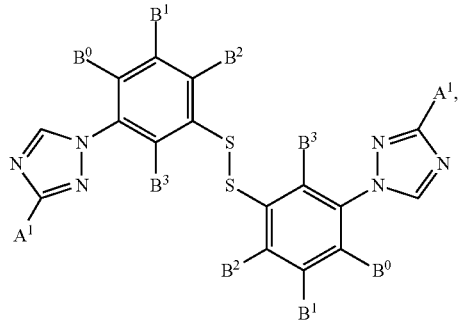

(II-A)

wherein
$A^1$ is trifluoromethyl;
$B^0$ is hydrogen, amino, halogen, cyano, nitro, alkyl, haloalkyl, alkylthio, haloalkylthio, alkoxy or haloalkoxy, and
$B^1$, $B^2$ and $B^3$ independently of one another are each hydrogen, halogen, cyano, nitro, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, alkoxycarbonylalkoxy, alkoxyalkoxy, alkylthio, haloalkylthio, alkoxyalkylthio, alkylsulphinyl, haloalkylsulphinyl, alkoxyalkylsulphinyl, alkylsulphonyl, haloalkylsulphonyl, alkoxyalkylsulphonyl, acyl, haloalkylcarbonyl, carboxyl, alkoxycarbonyl or $NR^3R^4$, where $R^3$ and $R^4$ independently of one another are hydrogen, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl, or $R^3$ and $R^4$, together with the N atom to which they are attached, may form an optionally substituted saturated or unsaturated, five- to eight-membered ring which is optionally interrupted by heteroatoms.

12. An agrochemical composition comprising the at least one 3-Triazolylphenyl-substituted sulphide, according to claim 1, of formula (I), or formula (I-A), or formula (I-B); and extenders and/or surfactants.

13. A process for preparing an agrochemical composition, comprising mixing the at least one 3-Triazolylphenyl-substituted sulphide, according to claim 1, of formula (I), or formula (I-A), or formula (I-B) with extenders and/or surfactants.

14. A method of controlling animal pests comprising applying the mixing the at least one 3-Triazolylphenyl-substituted sulphide, according to claim 1, of formula (I), or formula (I-A), or formula (I-B) to animal pests and/or their habitat.

15. A method of controlling animal pests, in the protection of materials and/or in the veterinary sector comprising applying the 3-Triazolylphenyl-substituted sulphide of formula (I) according to claim 1 to animal pests and/or to a habitat of the animal pests.

16. The 3-Triazolylphenyl-substituted sulphide according to claim 1 is a compound of the formula (I-A-1):

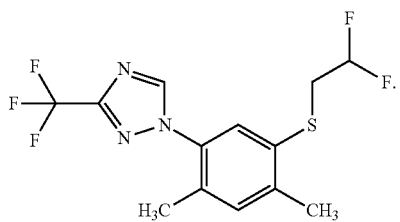 [SMILES: Cc1cc(C)c(-n2cnc(C(F)(F)F)n2)cc1SCC(F)F]

17. The process according to claim 6, wherein $A^1$ is $CF_3$, $B^0$ is $CH_3$, $B^1$ is H, $B^2$ is $CH_3$, $B^3$ is H, n is 0, $R^1$ is H and $R^2$ is $CHF_2$.

18. The process according to claim 7, wherein $A^1$ is $CF_3$, $B^0$ is $CH_3$, $B^1$ is H, $B^2$ is $CH_3$ and $B^3$ is H.

19. The process according to claim 8, wherein $A^1$ is $CF_3$, $B^0$ is $CH_3$, $B^1$ is H, $B^2$ is $CH_3$ and $B^3$ is H.

20. The active compound composition according to claim 9, wherein the 3-Triazolylphenyl-substituted sulphide is the compound of the formula (I-A-1).

21. The composition according to claim 10, wherein the 3-Triazolylphenyl-substituted sulphide is the compound of the Formula (I-A-1).

22. The disulphide of formula (II-A) according to claim 11, wherein $B^0$ is $CH_3$, $B^1$ is H, $B^2$ is $CH_3$ and $B^3$ is H.

23. The agrochemical composition according to claim 12, wherein the at least one 3-Triazolylphenyl-substituted sulphide is the compound of the formula (I-A-1).

24. The process according to claim 13, wherein the at least one 3-Triazolylphenyl-substituted sulphide is the compound of the formula (I-A-1).

25. The method according to claim 14, wherein the at least one 3-Triazolylphenyl-substituted sulphide is the compound of the formula (I-A-1).

26. The method according to claim 15, wherein the 3-Triazolylphenyl-substituted sulphide is the compound of the formula (I-A-1).

* * * * *